United States Patent [19]

Szilágyi et al.

[11] Patent Number: 4,613,615
[45] Date of Patent: Sep. 23, 1986

[54] DITHIOCARBAMATE PLANT FUNGICIDES

[75] Inventors: Gyula Szilágyi, Miskolc; Csaba Tar, Kazincbarcika; Mariann Bendly, Kazincbarcika; Erzsébet Dienes née, Mezo, Kazincbarcika; Gábor Boda, Kazincbarcika; János Csuták, Kazincbarcika, all of Hungary

[73] Assignee: Borsodi Vegyi Kombinat, Kazincbarcika, Hungary

[21] Appl. No.: 568,210
[22] PCT Filed: Apr. 20, 1983
[86] PCT No.: PCT/HU83/00017
 § 371 Date: May 21, 1984
 § 102(e) Date: May 21, 1984
[87] PCT Pub. No.: WO83/03603
 PCT Pub. Date: Oct. 27, 1983

[30] Foreign Application Priority Data

Apr. 20, 1982 [HU] Hungary .................. 1205/82

[51] Int. Cl.$^4$ .................. A01N 47/10; C07C 155/08
[52] U.S. Cl. .................. 514/478; 558/235; 558/236
[58] Field of Search .................. 260/455 A, 455 R; 424/300, 301; 514/478; 558/235, 236

[56] References Cited

U.S. PATENT DOCUMENTS 3,352,815 11/1967 Bencze .................. 260/455 A

FOREIGN PATENT DOCUMENTS 1038727 8/1966 United Kingdom .......... 260/455 A
1314392 4/1973 United Kingdom .......... 260/455 A
1395657 5/1975 United Kingdom .......... 260/455 A Primary Examiner—Henry R. Jiles
Assistant Examiner—Robert C. Whittenbaugh
Attorney, Agent, or Firm—Karl F. Ross; Herbert Dubno

[57] ABSTRACT

The invention relates to a plant protecting composition which contains 1 to 80% by weight substituted alkoxycarbonyl dithiocarbamates or thiolcarbamates of formula (I)

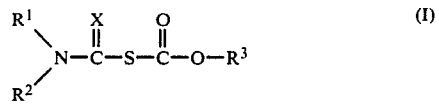

wherein
 $R^1$ and $R^2$ are the same or different and stand for hydrogen, straight or branched chain, saturated or unsaturated alkyl, alkoxyalkyl, alkylaminoalkyl, dialkylaminoalkyl having 1 to 10 carbon atoms, cycloalkyl, phenyl or halogenphenyl,
 $R^3$ stands for straight or branched chain, saturated or unsaturated alkyl, cycloalkyl, phenyl or halogenphenyl, and
 X stands for oxygen or sulfur,
as well as 10 to 90% by weight solid and/or liquid diluent(s) and 1 to 30% by weight additive(s).

The novel compounds of formua (I) may be obtained in such way that a salt of disubstituted dithiocarbamic acid or thiolcarbamic acid of formula (II)

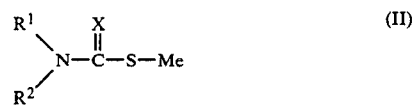

wherein $R^1$, $R^2$ and X have the same meanings as defined above and Me stands for alkali or ammonium ion or amine residue, is reacted with a chloroformic acid ester of formula (III)

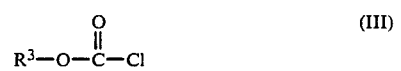

in an organic solvent or in aqueous medium at a temperature of 0° C. to 60° C. thereafter the compound of formula (I) is obtained by a method known per se.

7 Claims, No Drawings

DITHIOCARBAMATE PLANT FUNGICIDES

The invention relates to plant protecting composition which contains 1 to 80% by weight substituted alkoxycarbonyl dithiocarbamates or thiolcarbamates of formula (I)

$$\begin{array}{c} R^1 \\ \phantom{R^1}\diagdown \\ \phantom{R^1R^2}N-\underset{\underset{\displaystyle }{\|}}{\overset{\overset{\displaystyle X}{\|}}{C}}-S-\underset{\underset{\displaystyle }{\|}}{\overset{\overset{\displaystyle O}{\|}}{C}}-O-R^3 \\ \phantom{R^1}\diagup \\ R^2 \end{array} \quad (I)$$

wherein
 $R^1$ and $R^2$ are the same or different and stand for hydrogen, straight or branched chain, saturated or unsaturated alkyl, alkoxyalkyl, alkylaminoalkyl, dialkylaminoalkyl having 1 to 10 carbon atoms, cycloalkyl, phenyl or halogenphenyl,
 $R^3$ stands for straight or branched chain, saturated or unsaturated alkyl, cycloalkyl, phenyl or halogenphenyl, and
 X stands for oxygen or sulfur,
as well as 10 to 90% by weight solid and/or liquid diluent(s) and 1 to 30% by weight additive(s).

A further feature of the invention is a process for the preparation of the novel substituted alkoxycarbonyl dithiocarbamates or thiolcarbamates of formula (I).

An essential field of the modern plant protection on a large-scale is chemical plant protection. Thus it can be prevented, that a variety of pests can ruin a great part of the harvest. In the last few years many plant protecting compositions were used in the practice against the fungal pests of the cultivated plants. The use of these compositions resulted, however, in some resistance. So novel compositions should be found by which the rotation of the composition may be assured and the resistant fungi may be killed.

In the 1950s and 1960s dithiocarbamates were found to be useful against several fungal pests, e.g. branches Botrytis, *Phytophtora infestans* and *Venturia inaeqailia* (U.S. Pat. Nos. 2,457,674 and 2,974,156 and GBP No. 996,264). These are not systemic fungicides so repeated spraying is necessary.

Fungicidal S-alkyl dithiocarbamates are also known (U.S. Pat. No. 2,695,901). The disadvantage of these fungicides is that they cannot be used in every culture and owing to the resistance increasing doses are needed.

In view of the above described novel plant protecting compositions should be found which do not show the disadvantages of the known compositions and the rotation of the composition being necessary for the safe production may be solved.

It was found that the known disadvantages of the fungicidal dithiocarbamates may be eliminated when a composition is used which contains 1 to 80% by weight substituted alkoxycarbonyl dithiocarbamate and/or thiolcarbamate of formula (I), 10 to 90% by weight solid and/or liquid diluent(s) and 1 to 30% by weight additive(s), preferably tensides.

The meaning of the substituents in the substituted alkoxycarbonyl dithiocarbamates or thiolcarbamates may be the following: $R^1$ and $R^2$ may be the same or different and may stand for straight or branched chain, saturated or unsaturated alkyl, alkoxyalkyl, alkylaminoalkyl, dialkylaminoalkyl having 1 to 10 carbon atoms, cycloalkyl, phenyl or halogenphenyl; $R_3$ may stand for straight or branched chain, saturated or unsaturated alkyl, cycloalkyl, phenyl of halogenphenyl and X may stand for oxygen or sulfur.

The composition of the invention may be used e.g. against the pests *Fusarium graminearum*, branches Botrytis, *Phytopthora infestans, Venturia inaequalia* and cause no damaging effects in the cultivated plants.

A feature of the invention is the process for the preparation of the substituted alkoxycarbonyl dithiocarbamates and thiolcarbamates of formula (I). According to this process the compounds of the invention are prepared in such a way that a salt of a disubstituted dithiocarbamic acid or thiolcarbamic acid of formula (II)

$$\begin{array}{c} R^1 \\ \phantom{R^1}\diagdown \\ \phantom{R^1R^2}N-\underset{\underset{\displaystyle }{\|}}{\overset{\overset{\displaystyle X}{\|}}{C}}-S-Me \\ \phantom{R^1}\diagup \\ R^2 \end{array} \quad (II)$$

wherein
 $R^1$, $R^2$ and X have the same meanings as defined above and
 Me stands for alkali or ammonium ion or amine residue, is reacted with a chloroformic acid ester of formula (III)

$$R^3-O-\underset{\underset{\displaystyle }{\|}}{\overset{\overset{\displaystyle O}{\|}}{C}}-Cl \quad (III)$$

preferably in aqueous medium at a temperature of 0° C. to 60° C.

The preparation of the compounds of formula (I) is further shown in the following Examples.

EXAMPLE 1

56.4 g (0.25 moles) of diethyl dithiocarbamic acid sodium $\times 3H_2O$ and 250 ml of water are charged into a 500 ml round-bottom flask equipped with a stirrer, thermometer and feed hopper thereafter 30.7 g of chloroformic acis isopropyl ester are added at 5° to 10° C. for 30 minutes. The reaction mixture is stirred further for 30 minutes at 10° C. then the N,N-diethyl-S-isopropyloxycarbonyl dithiocarbamate obtained as an oily phase is separated and dried over sodium sulfate. So 38 g of product are obtained. Yield 64.6%, $n_D^{20}=1.4800$.

EXAMPLE 2

20 g (0.1 mole) of N,N-dimethylaminopropyl dithiocarbamic acid sodium and 70 ml of water are charged into a 250 ml round-bottom flask equipped with a stirrer, thermometer and feed hopper thereafter 12.2 g of chloroformic acid isopropyl ester are added at a temperature below 10° C. during 1 hour and the reaction mixture is stirred further for 30 minutes. The product obtained as pale yellow crystals is filtered on a glass filter, washed with $2\times 20$ ml of water and dried. So 19.6 g N,N-dimethylaminopropyl-S-isopropyloxycarbonyl dithiocarbamate are obtained. Yield 74%, m.p. 96° C.

Further compounds of the invention are produced by the processes as described in Examples 1 and 2. These compounds are enumerated in Table I where the corresponding physical constants are also stated.

TABLE I

| No. | $R^1$ | $R^2$ | X | $R^3$ | m.p. | Physical constant $n_D^{20}$ |
|---|---|---|---|---|---|---|
| 1 | ethyl | ethyl | S | isopropyl |  | 1.4800 |

TABLE I-continued

| No. | R¹ | R² | X | R³ | m.p. | $n_D^{20}$ |
|---|---|---|---|---|---|---|
| 2 | dimethylaminopropyl | H | S | isopropyl | 96° C. | |
| 3 | methyl | methyl | S | isopropyl | 56.4–58° C. | |
| 4 | isononyloxypropyl | H | S | isopropyl | | 1.4940 |
| 5 | methoxyethyl | H | S | isopropyl | | 1.4880 |
| 6 | ethoxypropyl | H | S | isopropyl | | 1.4748 |
| 7 | allyl | allyl | S | isopropyl | | 1.5385 |
| 8 | allyl | H | S | isopropyl | | 1.5448 |
| 9 | allyl | allyl | S | n-propyl | | 1.5490 |
| 10 | allyl | allyl | S | n-butyl | | 1.5236 |
| 11 | methoxyethyl | H | S | n-propyl | | 1.4828 |
| 12 | allyl | H | S | n-propyl | | 1.5460 |
| 13 | allyl | H | S | n-butyl | | 1.5168 |
| 14 | methyl | methyl | S | n-propyl | | 1.5210 |
| 15 | allyl | allyl | S | methyl | | 1.5780 |
| 16 | allyl | H | S | methyl | | 1.5350 |
| 17 | ethyl | ethyl | S | methyl | | 1.5650 |
| 18 | ethyl | ethyl | S | n-propyl | | 1.5225 |
| 19 | ethyl | ethyl | S | n-butyl | | 1.4280 |
| 20 | methyl | methyl | S | methyl | | 1.5798 |
| 21 | methyl | methyl | S | n-butyl | | 1.4170 |
| 22 | isononyloxypropyl | H | S | methyl | | 1.4672 |
| 23 | isononyloxypropyl | H | S | n-propyl | | 1.4860 |
| 24 | isononyloxypropyl | H | S | n-butyl | | 1.4922 |
| 25 | dimethylaminopropyl | H | S | methyl | | 1.5215 |
| 26 | dimethylaminopropyl | H | S | n-propyl | | |
| 27 | dimethylaminopropyl | H | S | n-butyl | | |
| 28 | cyclohexyl | H | S | methyl | | |
| 29 | cyclohexyl | H | S | n-propyl | | 1.5862 |
| 30 | cyclohexyl | H | S | isopropyl | | |
| 31 | cyclohexyl | H | S | n-butyl | | |
| 32 | dimethylaminopropyl | H | S | ethyl | 135° C. | |
| 33 | cyclohexyl | H | S | ethyl | | 1.5432 |
| 34 | methyl | methyl | S | ethyl | | 1.5380 |
| 35 | allyl | allyl | S | ethyl | | 1.5605 |
| 36 | allyl | H | S | ethyl | | 1.5135 |
| 37 | isononyloxypropyl | H | S | ethyl | | 1.4772 |
| 38 | butoxypropyl | H | S | methyl | | 1.4800 |
| 39 | butoxypropyl | H | S | ethyl | | 1.5095 |
| 40 | butoxypropyl | H | S | isopropyl | | 1.4780 |
| 41 | butoxypropyl | H | S | n-propyl | | 1.5080 |
| 42 | butoxypropyl | H | S | butyl | | 1.5045 |
| 43 | dimethylaminopropyl | H | S | methyl | | 1.5215 |
| 44 | dimethylaminopropyl | H | S | n-butyl | | 1.4805 |
| 45 | ethyl | ethyl | O | methyl | | 1.4552 |
| 46 | ethyl | ethyl | O | ethyl | | 1.4330 |
| 47 | ethyl | ethyl | O | n-propyl | | 1.4245 |
| 48 | ethyl | ethyl | O | iso-propyl | | 1.4130 |
| 49 | methyl | methyl | S | 2-chlorophenyl | | 1.5772 |
| 50 | isononyloxypropyl | H | S | 2-chlorophenyl | | 1.5081 |
| 51 | butoxypropyl | H | S | 2-chlorophenyl | | 1.5292 |
| 52 | methyl | methyl | O | 2-chlorophenyl | | 1.5450 |

The plant protecting composition according to the invention may be applied as emulsifiable concentrate. The preparation of the composition is shown in the following Examples.

EXAMPLE 3

Into 250 ml round-bottom flask equipped with a stirrer 20 g N,N-dimethyl-S-isopropyloxycarbonyl ditiocarbamate, 70 g kerosine, thereafter 5 g Tensiofix IS and 5 g Tensiofix AS emulsifiers are charged. The reaction mixture is stirred till the total solution. So a 20% emulsifiable concentrate is obtained.

In Table II emulsifiable concentrates prepared as described in Example 3 are given.

TABLE II

| | | Components (parts by weight) | | | | | |
|---|---|---|---|---|---|---|---|
| No. according to Table I | Compound according to Table I | Kerosine | Xylole | Dichloromethane | Tensiofix IS | Tensiofix AS | Composition |
| 12 | 20 | 76 | | | 2 | 2 | 20 EC |
| 15 | 20 | 76 | | | 2 | 2 | 20 EC |
| 5 | 20 | 76 | | | 2 | 2 | 20 EC |
| 7 | 20 | 76 | | | 2 | 2 | 20 EC |
| 4 | 20 | 76 | | | 2 | 2 | 20 EC |
| 14 | 20 | 76 | | | 2 | 2 | 20 EC |
| 9 | 20 | 76 | | | 2 | 2 | 20 EC |
| 12 | 50 | | 30 | 10 | 5 | 5 | 50 EC |
| 12 | 30 | | 60 | | 5 | 5 | 30 EC |

The fungal pests of the cultivated plants may be killed by using the composition of the invention containing 1 to 80% by weight substituted alkoxycarbonyl dithiocarbamate or thiolcarbamate of formula (I), 10 to 90% by weight of solid and/or liquid diluent(s), as well as 1 to 30% by weight additive(s). The biological test performed with the compositions according to the invention are shown below.

EXAMPLE 4

While preparing the nutrient medium of the fungus (1 liter of which contains 200 g corn meal, 20 g agar-agar and 150 g saccharose) such amount of the active ingredients is mixed homogenously with the nutrient medium having been not cooled yet and so being still liquid that the concentration of the active ingredient in the nutrient medium should be 500, 50 or 5 ppm. From the nutrient mediums so obtained thin plates are poured in Petri dishes and after the nutrient medium has been setted solid every Petri dishes were infected with each 4 *Fusarium graminearum* fungus inoculum. The inoculums were fungus cultures having a diameter of 6 mm which were cut out from the culture of the fungus being grown on agar-agar for 8 to 10 days under sterile conditions. A nutrient plate, into which no substance to be examined was admixed, was also inoculated and this was considered as the control. Each concentration of each substance was examined in 4 series and the results obtained were averaged.

Evaluation: 6 to 8 days after the inoculation the diameter of the colony of *F. graminearum* was measured round each inoculum. The % of inhibition of the growing of the mycel colony caused by the treatments was calculated. The diameters of the fungus colonies grown on untreated agar-agar plates were considered as 100%. The % of inhibition is characteristic for the effectiveness of the composition.

EXAMPLE 5

The solutions of the active ingredients in aqueous solvent were poured onto the sterile nutrient medium plates being in Petri dishes. The concentration of the active ingredients was 1000, 100 and 10 ppm. Onto each nutrient medium having a diameter of 90 mm 2 ml solution was poured. The solvent used was ethanol or acetone. The solvents evaporated from the Petri dishes being covered and placed under air-extractor during 1 day. After the evaporation of the solvent the Petri dishes were inoculated with *F. graminearum* as stated above and cultivated at 25° C. The results were evaluated as in case of the poisoned agar.

The fungicidal effectiveness of the compounds of the invention is shown in Table III.

TABLE III

| No. according to Table I | Concentration (ppm) | % of inhibition of the growing of the mycel (fungicidal effectiveness) |
|---|---|---|
| 3 | 500 | 100 |
|   | 50 | 64 |
|   | 5 | 41 |
| 4 | 500 | 100 |
|   | 50 | 80 |
|   | 5 | 24 |
| 5 | 1000 | 100 |
|   | 100 | 100 |
|   | 10 | 39 |
| 7 | 1000 | 100 |
|   | 100 | 100 |
|   | 10 | 32 |
| 8 | 1000 | 100 |
|   | 100 | 100 |
|   | 10 | 46 |
| 9 | 1000 | 100 |
|   | 100 | 100 |
|   | 10 | 19 |
| 14 | 1000 | 100 |
|   | 100 | 100 |
|   | 10 | 12 |
| 15 | 1000 | 100 |
|   | 100 | 100 |
|   | 10 | 4 |

We claim:

1. A compound of the Formula (I)

$$\begin{array}{c} R^1 \\ \phantom{R^1}\diagdown \\ \phantom{R^1R^2}N-\underset{\underset{S}{\|}}{C}-S-\underset{\underset{O}{\|}}{C}-O-R^3 \\ \phantom{R^1}\diagup \\ R^2 \end{array}$$

wherein $R^1$ is methyl, ethyl, allyl, dimethylamino-propyl, isononyloxypropyl, methoxyethyl, ethoxypropyl, cyclohexyl, or butoxypropyl;

$R^2$ is hydrogen, methyl, ethyl or allyl; and $R^3$ is $C_1$–$C_4$ alkyl.

2. The compound of the Formula (I) defined in claim 1 which is:
   (a) N,N-dimethyl-S-isopropoxycarbonyl dithiocarbamate;
   (b) N-(isononyloxypropyl)-S-isopropoxycarbonyl dithiocarbamate;
   (c) N-methoxyethyl-S-isopropoxycarbonyl dithiocarbamate;
   (d) N,N-diallyl-S-isopropoxycarbonyl dithiocarbamate;
   (e) N-allyl-S-isopropoxycarbonyl dithiocarbamate;
   (f) N,N-diallyl-S-n-propoxycarbonyl dithiocarbamate;
   (g) N,N-dimethyl-S-n-propoxycarbonyl dithiocarbamate; and
   (h) N,N-diallyl-S-methoxycarbonyl dithiocarbamate.

3. A composition for the protection of plants against fungal infection which comprises:
   1 to 80% by weight of a compound of the Formula (I) as defined in claim 1, 10 to 90% by weight of a solid or liquid diluent, and 1 to 30% by weight of a tenside additive.

4. The composition defined in claim 3 wherein the liquid diluent is a water-immiscible solvent present in the composition in an amount of 20 to 90% by weight.

5. The composition defined in claim 3 wherein the fungal infection of the plant is caused by *Fusarium grainearum*, branches Botrytis, *Phytopthora infestans*, or *Venturia inaequalia*.

6. A method of treating a cultivated plant against fungal infection which comprises the step of treating the plant with a fungicidally effective amount of the compound of the Formula (I) as defined in claim 1.

7. A method of treating a cultivated plant against fungal infection as defined in claim 6 wherein the fungicidal infection is caused by *Fusarium graminearum*, branches Botrytis, *Phytopthora infestans*, or *Venturia inaequalis*.

* * * * *